United States Patent
Dara

(10) Patent No.: US 6,207,956 B1
(45) Date of Patent: Mar. 27, 2001

(54) METHOD AND APPARATUS FOR QUANTITATIVE DETERMINATION OF TURFGRASS COLOR

(75) Inventor: Syed Tazul Dara, Savage, MN (US)

(73) Assignee: The Toro Company, Minneapolis, MN (US)

( * ) Notice: Subject to any disclaimer, the term of this patent is extended or adjusted under 35 U.S.C. 154(b) by 0 days.

(21) Appl. No.: 09/148,011

(22) Filed: Sep. 4, 1998

(51) Int. Cl.$^7$ .............................. G01N 21/35; G01J 3/02; G06F 19/00

(52) U.S. Cl. ................... 250/341.8; 250/339.11; 250/340; 702/28; 702/81

(58) Field of Search .................... 250/339.11, 339.07, 250/339.01, 340, 341.8; 702/28, 76, 81

(56) References Cited

U.S. PATENT DOCUMENTS

| | | | |
|---|---|---|---|
| 4,560,275 | * | 12/1985 | Goetz .................................. 356/326 |
| 4,866,644 | | 9/1989 | Shenk et al. .................... 364/571.02 |
| 4,969,739 | * | 11/1990 | McGee ................................ 351/124 |
| 5,793,035 | * | 8/1998 | Beck et al. ........................ 250/222.1 |
| 5,798,526 | * | 8/1998 | Shenk et al. .................... 250/339.09 |
| 5,822,219 | * | 10/1998 | Chen et al. ............................ 702/27 |
| 5,965,888 | * | 10/1999 | Engstrom et al. .............. 250/339.09 |

OTHER PUBLICATIONS

"BioPro™ Tournament Greens", The Toro Company, Bloomington, MN; 4 pgs (Aug. 1994).
"Minolta—Spectrophotometer CM–500 Series", Minolta Co., Ltd.; 8 pgs (1994).
"Minolta—Precise Color Communication", Minolta Co., Ltd.; pp. 1–49 (1994).

* cited by examiner

Primary Examiner—Constantine Hannaher
Assistant Examiner—Albert J. Gagliardi
(74) Attorney, Agent, or Firm—Merchant & Gould P.C.

(57) ABSTRACT

The present invention discloses testing turfgrass samples in a spectrophotometer. The resulting color output is provided to a processor for determining the quantitative color scale. The resultant output of the processor might be a single number 1 through 9—depending on the relative "greenness" of the tested turfgrass. To determine the standardized number, the processor compares the received color output from the spectrophotometer to a first stored set of values. Additionally, the received color output can be compared to a second stored set of values to predictively determine if adjusting certain nutrients, water, fertilizer, etc. will result in beneficial or other desired results in the turf. The first and second stored set of values or data is empirically established. In addition, a sealed turfgrass sample as a check or calibration sample, in connection with the use of NIRS equipment to determine instrument performance. The daily use of sealed turfgrass check samples allows the operators to determine the instrument performance and monitor deterioration of the turfgrass check sample. The variability is then incorporated in the future calibration to improve the accuracy and the validity of the NIRS measurements.

3 Claims, 22 Drawing Sheets

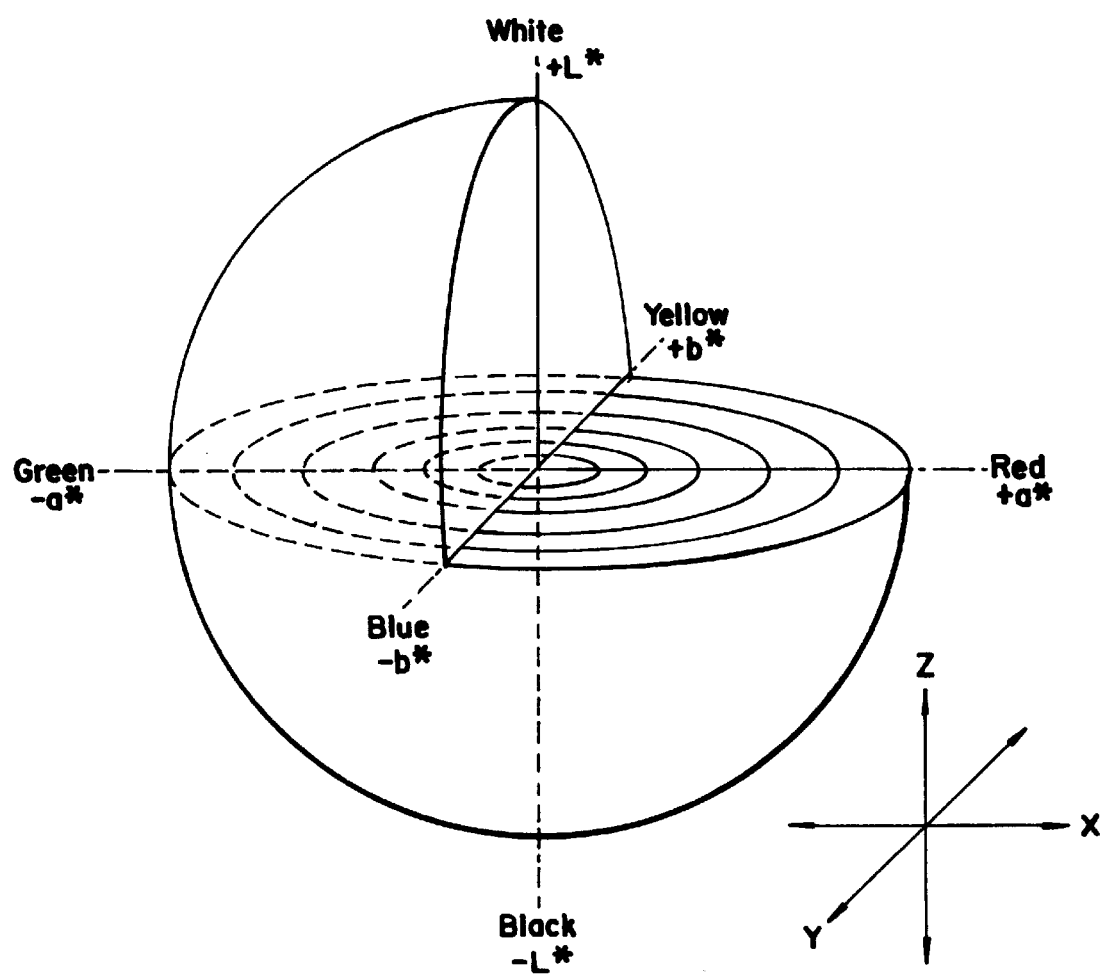

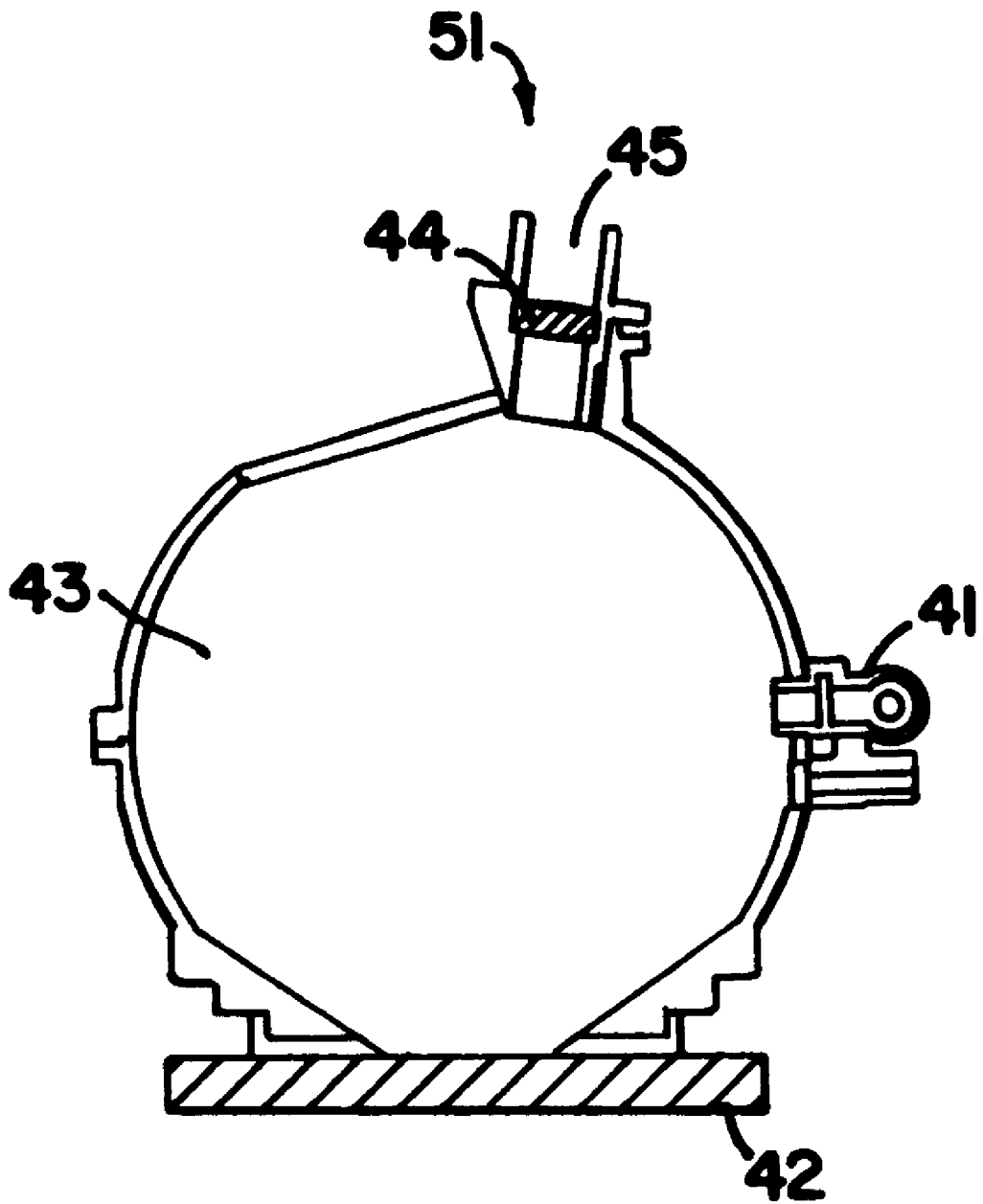

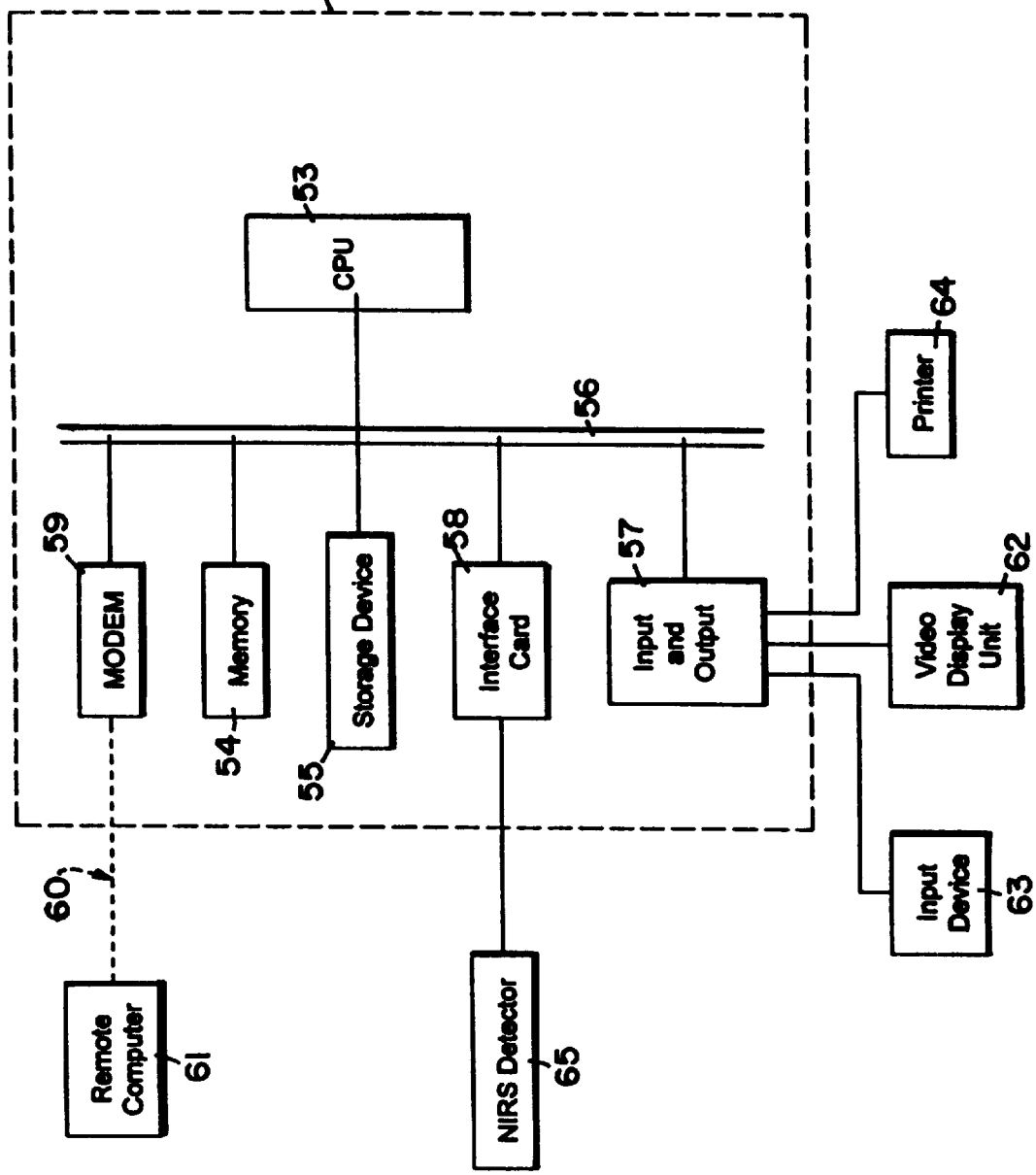

FIG. 9a

Diagnostic Services

AGRONOMICS                                                    NIRS Tissue Analysis Report

| XYZ Golf Course | Toro Agronomics System |
|---|---|

Sample Date: 7/24/98  Grass Type: Bentgrass, Creeping
Sample Number: 123  Sample Location: Green 6 7-24-98

| Nutrient | N % | P % | K % | Ca % | Mg % | S % |
|---|---|---|---|---|---|---|
| Target High | 6.00 | 0.60 | 2.60 | 0.75 | 0.30 | 0.50 |
| ** TEST | 4.36 | 0.54 | 2.88 | 0.42 | 0.25 | 0.43** |
| Target Low | 4.50 | 0.30 | 2.20 | 0.50 | 0.25 | 0.25 |

| Element | Color | Fe ppm | Zn ppm | Mn ppm | Cu ppm | B ppm |
|---|---|---|---|---|---|---|
| Target High | 9 (Excellent) | 300 | 75 | 100 | 30 | 20 |
| ** TEST | 6.02 | 10 | 53 | 82 | 15 | 7** |
| Target Low | 1 (Poor) | 100 | 25 | 50 | 8 | 8 |

FIG. 9c

NIRS TREND ANALYSIS
TORO DIAGNOSTIC SERVICES
-Bentgrass, Creeping- Chipping Green 7/22/98

Diagnostic Services
AGRONOMICS

| Constituent | XYZ Golf Course 06/09/98 | 06/11/98 | 06/17/98 | 06/24/98 | 07/01/98 | 07/08/98 | 07/15/98 | 07/22/98 | TARGET RANGE |
|---|---|---|---|---|---|---|---|---|---|
| Nitrogen, % | 5.71 | 5.12 | 5.35 | 5.42 | 5.39 | 5.18 | 5.60 | 5.59 | (4.50 - 6.00) |
| Phosphorous, % | 0.66 | 0.54 | 0.63 | 0.60 | 0.60 | 0.58 | 0.64 | 0.66 | (0.30 - 0.60) |
| Potassium, % | 2.26 | 2.32 | 2.12 | 2.32 | 2.07 | 2.39 | 2.16 | 2.34 | (2.20 - 2.60) |
| Calcium, % | 0.65 | 0.42 | 0.48 | 0.47 | 0.49 | 0.49 | 0.53 | 0.49 | (0.50 - 0.75) |
| Magnesium, % | 0.29 | 0.21 | 0.23 | 0.21 | 0.23 | 0.22 | 0.24 | 0.26 | (0.25 - 0.30) |
| Sulfur, % | 0.62 | 0.52 | 0.55 | 0.55 | 0.55 | 0.49 | 0.58 | 0.60 | (0.25 - 0.50) |
| Zinc, ppm | 67.72 | 63.33 | 68.02 | 69.81 | 67.91 | 63.60 | 72.47 | 68.36 | (25.00 - 75.00) |
| Copper, ppm | 26.08 | 20.45 | 24.08 | 25.66 | 22.84 | 18.81 | 24.78 | 16.99 | (8.00 - 30.00) |
| Iron, ppm | 465.82 | 311.83 | 415.18 | 427.60 | 371.25 | 207.40 | 384.20 | 80.45 | (100.00 - 300.00) |
| Manganese, ppm | 131.70 | 112.15 | 118.51 | 116.57 | 118.60 | 105.90 | 123.57 | 128.65 | (50.00 - 100.00) |
| Boron, ppm | 9.96 | 4.50 | 4.43 | 3.58 | 4.49 | 8.02 | 5.25 | 5.26 | (8.00 - 20.00) |
| Color Index | 8.32 | 8.03 | 8.85 | 7.84 | 7.90 | 7.80 | 8.58 | 8.63 | |

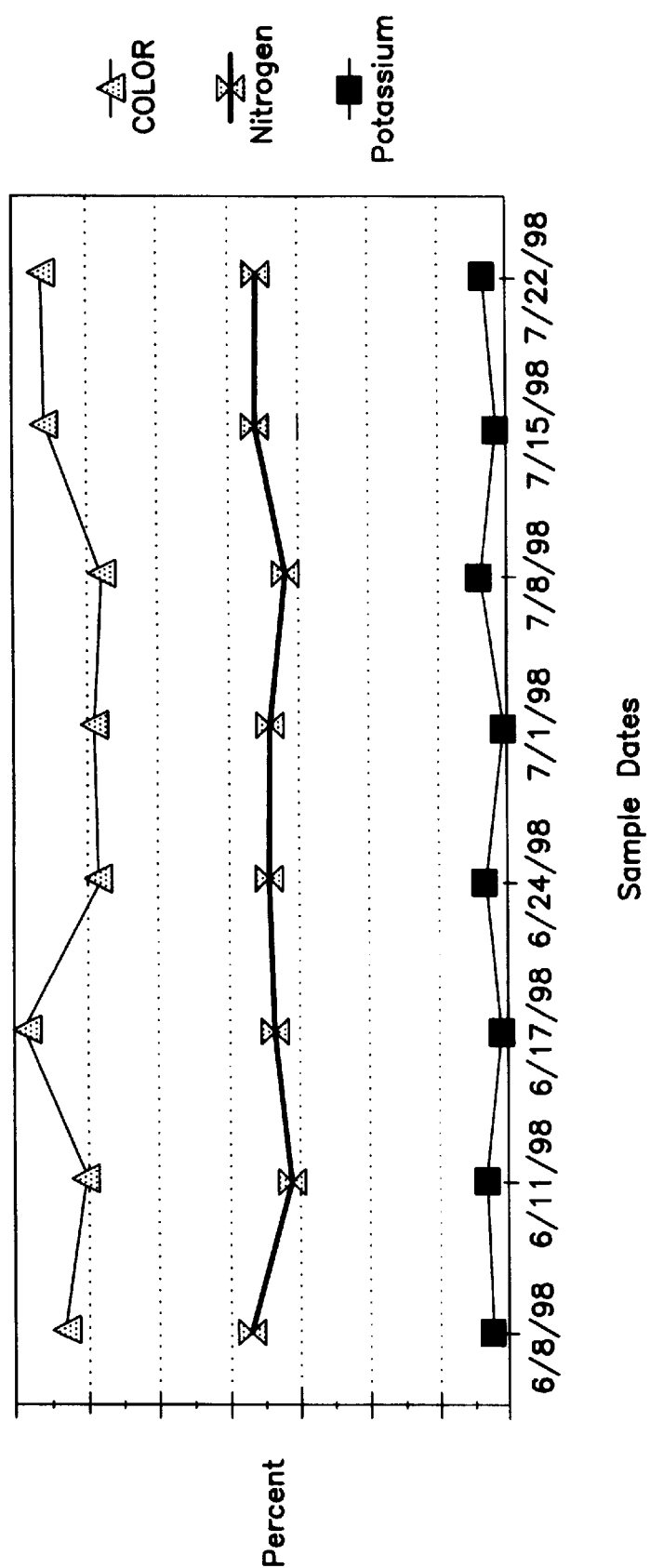

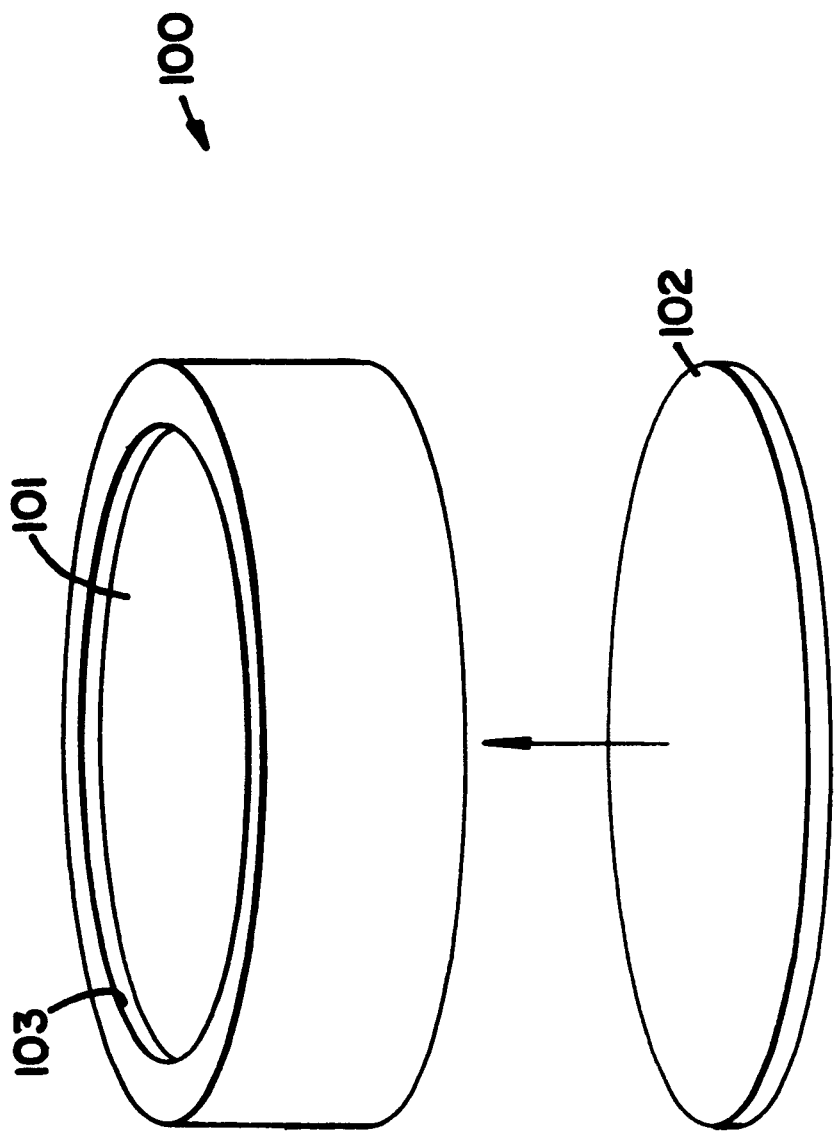

METHOD AND APPARATUS FOR QUANTITATIVE DETERMINATION OF TURFGRASS COLOR

FIELD OF THE INVENTION

This invention relates to analyzing turfgrass, more particularly to analyzing the color of turfgrass, and more particularly still to quantify the color of turfgrass using near infrared reflectance spectroscopy ("NIRS").

BACKGROUND

Turfgrass is widely used in landscaping, as a ground cover, and as a playing surface. For example, turfgrass is commonly found in parks, business landscaping, and suburban lawns. Examples of playing surfaces which utilize turfgrass include soccer and golf. This wide use of turfgrass is due in part to the many species of turfgrass and the concomitant variation in the characteristics and properties of the species.

It will be appreciated that the relative importance of any given property of turfgrass depends on both the species and application. Illustrative properties include the lushness or thickness, the texture, and the color of the grass. Of these properties, color is thought to be a particularly good indicator of the health of the turf. Accordingly, color is considered not only a key property—in and of itself as an aesthetic characteristic—but is also symptomatic of the overall health of the turfgrass. In view of this importance, the color of the grass is often closely monitored in many settings in which turfgrass is used.

Determining the color of turf to date has been a highly subjective exercise. The common method is for turf managers to use a scale of 1 to 9 with higher numbers corresponding to "greener" colors. Thus, in this system a poor yellow/brown color would be indicated with a "1" while an excellent dark green color would be indicated with a "9". While the system may qualitatively provide insight into the relative health of the grass, it has significant drawbacks. More specifically using this methodology, the "rated color" of the turf can vary depending on the health of the turf, the angle of the sun, the cloudiness, the presence or absence of dew, and the subjective perception of the viewer (e.g., what is "dark green" to one person may be "medium green" to another), among other factors. Additionally, color is generally recognized to have three major components: hue (red, yellow, green, blue, etc.); lightness (bright versus dark); and saturation (vivid versus dull). Given these three variables and the many terms used to express these variables, determining turf color is normally a highly subjective and inexact procedure.

Accordingly, there arises a need in the art to provide for an accurate apparatus and method which quantitatively measures turfgrass color on a consistent basis. Making such color measurements is known in other fields. One example is in paint mixing equipment. In that area, calorimetric techniques have previously been used to determine with some precision the hue, lightness and saturation of colors. Also, devices known as spectrophotometers have been constructed to measure color. A specific example of a spectrophotometer is manufactured by Minolta Company, Ltd., of Osaka Japan, under the model designation CM-525i series. The device uses a xenon arc lamp which is pulsed after a sample is located in a sample target area. The pulsed light enters an integrating sphere resulting in diffuse illumination of the test object. Light reflects off of the test object back into the integrating sphere. A converging lens gathers the reflected light onto a spectral sensor. The output from the spectral sensor is processed such that the device provides specific, reproducible color data in one of the several different spectral reflectance nomenclatures (e.g., XYZ or L*a*b*, among others).

Finally, quantitative analysis of turfgrass is not new. For example, The Toro Company (the assignee of the present invention), has used near infrared equipment to analyze turfgrass nutritional composition. After proper calibration, the results of such an analysis provide turf managers with information relating to levels of nitrogen, potassium, magnesium, iron, etc. in the turfgrass. In this manner, an indication of whether or not the plant is suffering from certain deficiencies can be ascertained.

Another system, distributed by Karsten, Inc., used a near infrared device in an effort to predict mineral content of grass by using one equation for all grasses. However, because all grasses (even within the same variety, but from different geographical areas) do not respond the same with different chemical/mineral levels (relative to the color of the grass with the differing levels), such system had significant drawbacks.

Therefore, there arises a need in the art for a method of and apparatus for quantitatively determining the color of turfgrass based on various ecotypes. Additionally, there arises a need in the art for a method and apparatus for determining nutritional health of turfgrass and predicting outcomes of changing nutritional parameters associated with quantitatively determining the color of the turfgrass. The present invention provides such a method and apparatus, while addressing the problems described above.

SUMMARY

The present invention provides a method and apparatus for using NIRS technology to determine turf grass color. Such invention provides an additional benefit of NIRS study over and above the current quantitative analysis of mineral composition of turf grass. For example, quantitative detection of turfgrass color together with mineral composition analysis allows predictive results of variations in mineral parameters. Further, the use of individual equations minimizes the blurring which occurs when different varieties (and/or different geographical samples of the same or similar varieties) are placed together in the same statistical sample.

While the principles of the present invention will be described herein in connection with determining the color of turfgrass in a quantitative fashion, it should be understood that such use is illustrative of such a method and apparatus for quantitative color determination for other organic matter. For example, the principles of the present invention might be used with other types of ground covers, trees, crops, and the like. Accordingly, it should be appreciated that the principles of the present invention apply broadly to the real-time quantitative color measurement of organic matter.

In a preferred implementation of the present invention, a turfgrass sample is tested in a spectrophotometer. The resulting color output is provided to a processor for determining the quantitative color scale. Continuing with the turfgrass example, the resultant output of the processor might be a single number 1 through 9—depending on the relative "greenness" of the tested turfgrass. To determine the standardized number, the processor compares the received color output from the spectrophotometer to a first stored set of values. Additionally, the received color output can be compared to a second stored set of values to predictively determine if adjusting certain nutrients, water, fertilizer, etc.

will result in beneficial or other desired results in the turf. The first and second stored set of values or data is empirically established.

The invention also includes the use of a sealed turfgrass sample as a check or calibration sample, in connection with the use of NIRS equipment to determine instrument performance. The daily use of sealed turfgrass check samples allows the operators to determine the instrument performance and monitor deterioration of the turfgrass check sample. The variability is then incorporated in the future calibration to improve the accuracy and the validity of the NIRS measurements.

In the past, turf managers could not associate the visual color and the nutrition composition—despite known relationships (e.g., such as the application of nitrogen improves color). However, according to one feature of the present invention, turf managers are now provided with a virtual real-time trend analysis. The results of the analysis can be examined to evaluate the effect of current plant nutrition program(s) and to optimize the program(s) for better color and nutritional balance.

Another feature of the present invention is that large scale applications and other blanket applications of plant nutrients can be avoided. In the past, if the color-nutrient relationship was not known, blanket applications of unnecessary nutrients were provided to large areas which did not require such application and/or which did not exhibit improvement upon such application. Those skilled in the art will appreciate that non-point source pollution and leaching of nutrients to ground water is becoming an increasingly important issue and it is desirable to eliminate the run-off and leaching associated with such unnecessary or ineffective applications.

Therefore, according to one aspect of the invention, there is provided an apparatus for determining the color of a sample of turf grass, comprising: a device for measuring the near infrared reflectance spectroscopy of the sample turfgrass, the device generating a photometric output signal; first memory means for storing a first value set of data relating to the color of turfgrass; and processing means, operatively connected of the device and the first memory means, for receiving the generated output signal, comparing the received signal to the first value set of data, and determining a quantitative color value of the sample turfgrass.

According to another aspect of the invention, there is provided an apparatus as recited above and further including: second memory means for storing a second value set of data relating to a specific mineral content of turfgrass based on color; and wherein the processing means are operatively connected to the second memory means and compare the determined quantitative color value of the sample turfgrass to the data in the second value set of data to determine a predictive outcome of application of the specific mineral to the turfgrass.

According to yet another aspect of the invention, there is provided: a method for determining the color of a sample of turf grass, comprising the steps of: storing a first value set of data relating to the color of turfgrass; measuring the near infrared reflectance spectroscopy of the sample turfgrass; generating a photometric output signal; receiving the generated output signal; comparing the received signal to the first value set of data; and determining a quantitative color value of the sample turfgrass. The foregoing method may also include the steps of storing a second value set of data relating to a specific mineral content of turfgrass based on color; and comparing the determined quantitative color value of the sample turfgrass to the data in the second value set of data; and determining a predictive outcome of application of the specific mineral to the turfgrass. Still further, the foregoing method may also include the step of applying the specific mineral to the turfgrass based on the predictive outcome.

These and other advantages and features which characterize the present invention will be further described in the drawing and detailed description set forth below.

BRIEF DESCRIPTION OF THE DRAWINGS

In the drawing, wherein like numerals represent like components throughout the several views:

FIG. 1 diagrammatically illustrates a representation of color solid for L*a*b* color space.

FIG. 2 schematically illustrates a preferred CM-525i detector 51 for field sample measurements of growing grass.

FIG. 3 functionally illustrates the devices useful in practicing the present invention.

FIGS. 9a through 9b and FIGS. 9c through 9g make up representative parts of NIRS Tissue Analysis Reports and NIRS Trend Analysis Reports respectively.

FIG. 10 is an exploded schematic view of the test sample container 100 used in connection with the present invention.

DETAILED DESCRIPTION

Figure 4A:
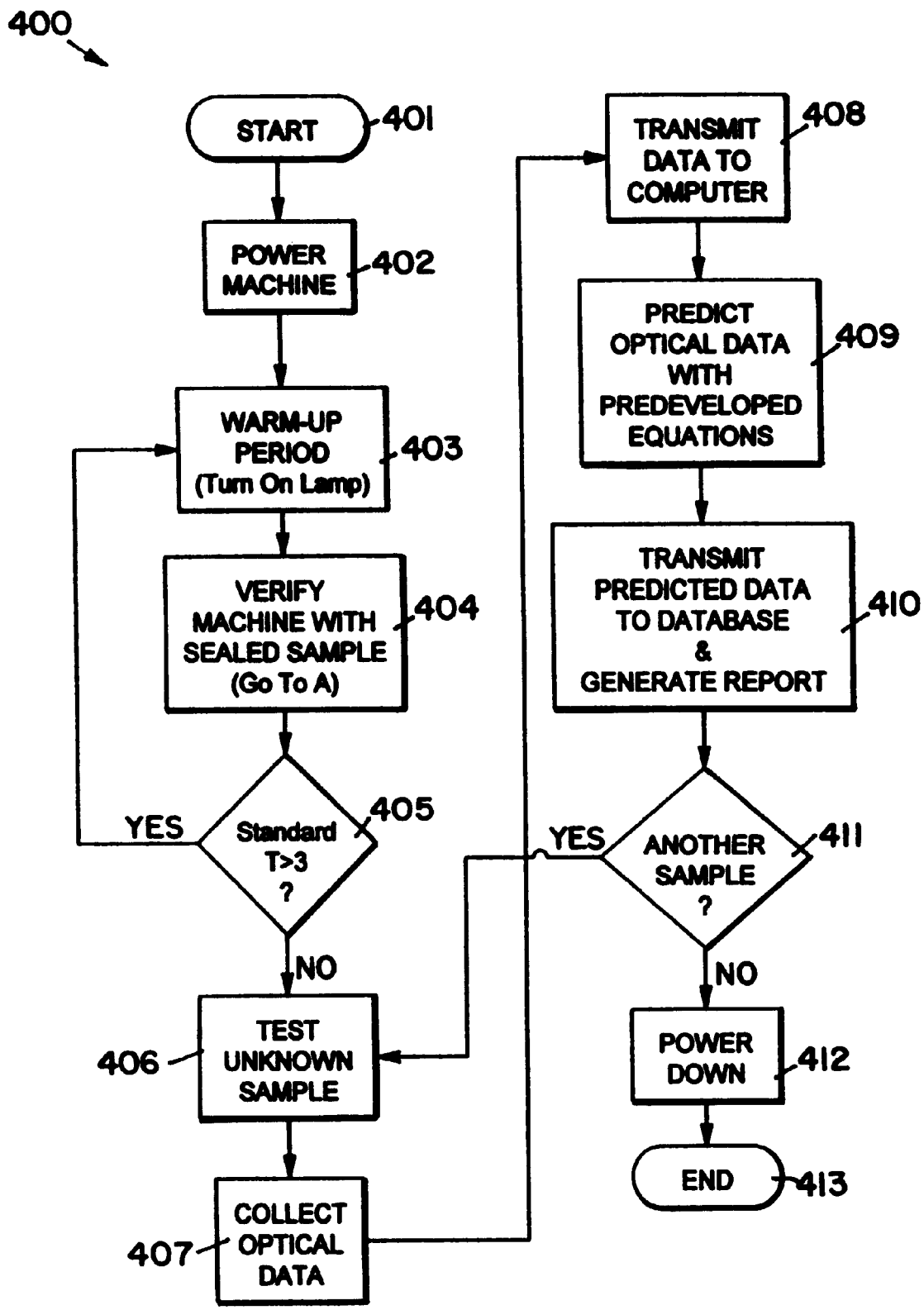
FIGS. 4a, 4b, and 4c set forth the logical programming steps which may be performed in analyzing a sample 42 of turf grass.

As indicated above, the principles of the present invention provides a method and apparatus for using NIRS technology to determine turf grass color. Such invention provides an additional benefit of NIRS study over and above the current quantitative analysis of mineral composition of turf grass. For example, quantitative detection of turfgrass color together with mineral composition analysis allows predictive results of variations in mineral parameters.

a. Spectral Nomenclature

Although a number of spectral reflectance nomenclatures might be used in connection with describing the present invention, the L*a*b* color space will be used herein. Table 1 below provides the definitions of the system.

TABLE 1

| Variable | Definition | Color |
|---|---|---|
| L* | lightness | — |
| a* | chromacity coordinate | — |
| +a* | | red direction |
| −a* | | green direction |
| b* | chromacity coordinate | — |
| +b* | | yellow direction |
| −b* | | blue direction |

As a further aid to understanding the CIELAB, or L*a*b* system, reference may be had to FIG. 1. In this figure the relationship of the system is illustrated. The a* and b* indicate color directions (e.g., in the x or y directions), with the center of the diagram being achromatic. Accordingly, as the a* and b* values increase, the designated point moves away from the center point and the saturation of the color increases. Overall, FIG. 1 illustrates the solid of the L*a*b* color space. Any flat plane (e.g., any plane which is parallel to an x-y plane) is a slice taken horizontally at a constant L* value. However, if a vertical slice is taken through the solid of the L*a*b* of FIG. 1, then a chromacity versus lightness graph results.

The description of a preferred apparatus and methods which may be used to practice the present invention will be deferred pending an overview of the theoretical background and empirical collection of data of the invention.

b. Theory of Invention and Empirical Collection of Data

The visible spectrum or color is defined as covering the spectral region between 400 and 700 nm. Currently NIRS technology utilizes wet chemistry or reference method measurements of essential minerals to develop statistical calibration models to predict mineral composition of unknown dry and ground turfgrass samples. However, the present invention provides a method and apparatus for a system in which the same principles can be applied to color with a suitable reference device. The device includes its own light source to measure specific optical intensity that relates to the "greenness" of growing turf color in the visible region of electromagnetic spectrum. This allows traditional method NIRS calibration development on the same dry and ground samples. It will be appreciated by those skilled in the art that the color changes of growing turfgrass to dry and ground samples must also be clearly understood. However, once the calibration model is established, the benefit is a consistent prediction of a quantitative color without the reference device. Overall, the method and apparatus allows the replacement of the currently used, subjective turf color measurement (e.g., by human perception) to an objective and repeatable method of turf color measurement.

To establish the necessary reference turfgrass, a laboratory sample is first established and is designated T3. The quantitative values for the T3 sample are:

L*=53.52
a*=−1.66
b*=11.88
ΔE=5.39.

Figure 11:
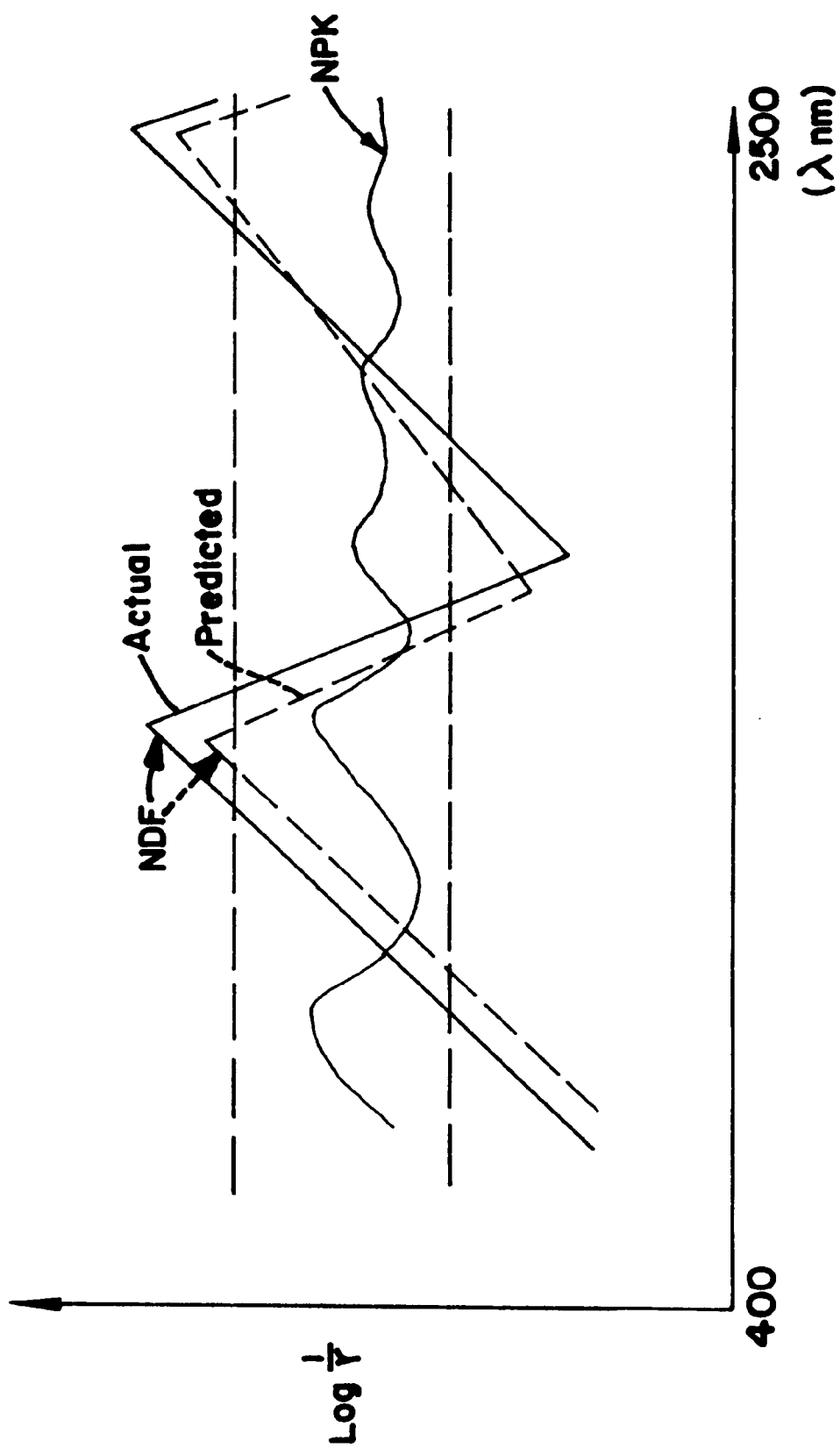
FIG. 11 is a diagrammatic representation of the larger coefficient swings of NDF used to fail a sample.

The purpose of the T3 sample is to measure all changes in turfgrass color with a fixed color scale or theoretically nonchanging color. An example calculation is as follows;

$$\Delta E^* ab = [(\Delta L^*)^2 + (\Delta a^*)^2 + (\Delta b^*)^2]^{1/2} \quad (1)$$

Where ΔL*, Δa*, Δb* is equal to the difference in L*a*b* values between the T3 color and the target color (i.e., in this case the target is an unknown turfgrass sample). As a safeguard, the output is compared to predicted result, wherein the student T test is larger than 3. Since it is easier to review the result predicted by an equation with larger coefficients, a parameter was specifically selected which exhibits such deviations. In the preferred embodiment, the Neutral Detergent Fiber (NDF) is used to demonstrate small deviations (i.e., because of larger coefficients). It will be appreciated that the Nitrogen, Phosphorous, Potassium (NPK) will tend to stay within a smaller range. FIG. 11 illustrates in a diagrammatic fashion the relative larger coefficients of NDF relative to NPK. This particular selection and use of NDF is unique since its selection is not generally of interest but is used to verify the instrument and check sample.

In order to arrive at the first data sets (color) and second data sets (relationship of color to various nutrients and other parameters—described in more detail below), a spectrophotometer is used in satellite locations where fresh turfgrass clippings are dried and then ground through a 1 mm screen before being presented to the device for composition analysis. Thus, the various NIRS calibration equations are empirically developed based on thousands of samples collected from various areas of the United States over several years. In the preferred embodiment, the instruments used to measure the NIRS color was a Minolta Spectrophotometer CM-525i having an output: ΔL, Δa, Δb, and ΔE. The NIRS equations are designed to take into consideration the turfgrass adaptation and variability by region and grass species. In a preferred embodiment, the resulting analytical report includes eleven (11) essential minerals analytical results with sufficiency ranges. However, any number of such results may be determined, analyzed, and/or predicted. Individual sample results are maintained to map out a trend analysis indicating the plant response of past nutrient application. This allows the turf managers to be judicious in application of plant nutrients.

The NIRS instrument measures reflectance at a specific band or wavelength in the near infrared region (700–3000 nm) of the electromagnetic spectrum.

Most quantitative reflectance analyses are done in 1100 to 2500 nm region. Preferably, the instruments at the satellite locations each have similar capabilities.

Multiple instruments used for turfgrass tissue analysis at different locations constitute a network. Even if instruments are set to the manufacturer's specification, their spectra are not alike enough to allow consistent prediction among the several instruments. Instrument standardization is the procedure to make the necessary correction to the spectrum of a host instrument. While those of skill in the art may well appreciate how such standardization is achieved, one procedure for accomplishing optical instrument calibration for field instruments is described in Shenk et al. (U.S. Pat. No. 4,866,644) which is incorporated herein by reference. In the preferred embodiment, instrument performance is tested daily with a sealed turf check cell, established by a set protocol to optimize the quality of the measurements.

One important aspect of NIRS is the organization of the calibration spectra. Factors affecting near infrared spectral signature of a turfgrass must be represented in the calibration set. These factors include the turfgrass sample's physical and chemical characteristics as influenced by species and region, method of preservation, processing, instrument type, sample environment—temperature, and humidity. Calibration equations are a mathematical relationship between spectra generated by instrument and analytical results obtained from a wet laboratory reference method, hence the need and use of the laboratory master instrument.

The following table 2 illustrates the methodology used in connection with the collection of samples.

TABLE 2

Field measurements for growing turfgrass color measurement, 2 locations, 3 applications, over a period of 15 weeks, 2 growing seasons and using a Minolta Spectrophotometer CM-525i having an output: ΔL, Δa, Δb, and ΔE Step 1

Field; Mow to collect clippings. Soil sampled and water sampled every observation day.

Step 2

Laboratory Method: Remove foreign material from clippings, measure color and repeat the same process after drying to 95% dry matter.

Step 3

Laboratory Method: Pass dry clipping through 1 mm screen using Udymill. Pack samples into sample cup with quartz crystal window for final color measurement and NIRS analysis.

Step 4

Laboratory Method: Pack sample cups for collecting NIRS spectrum (400–2500 nm) using NIR System Model 6500. Collect optical data in log 1/reflectance form.

Figure 6:
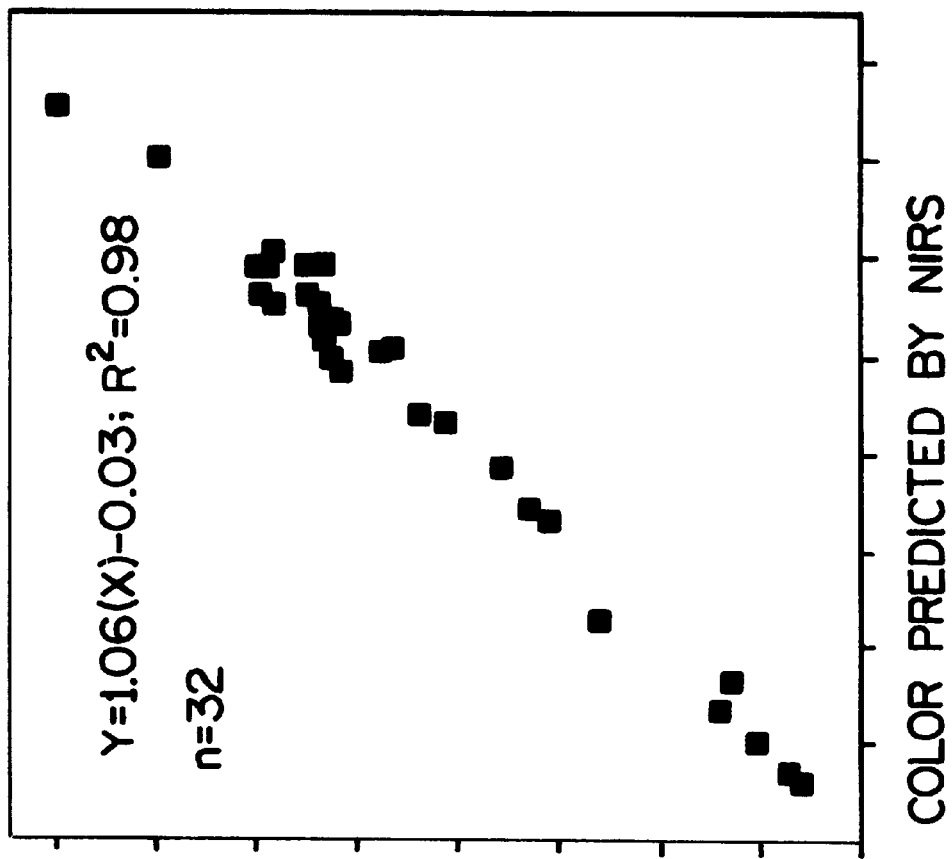
FIG. 6 is a graph illustrating the strong correlation between NIRS measurements and delta E.

The resulting data from samples collected in accordance with Table 2 indicates that the analytical results are accurate and reproducible under field conditions. FIG. 6 graphically illustrates the correlation between NIRS measurements and delta E output by the Minolta CM-525i. As noted above, the present invention also includes the use of a sealed turfgrass sample as a check or calibration sample, in connection with the use of NIRS equipment to determine turfgrass color. The daily use of sealed turfgrass check samples allows the operators to determine the instrument performance and monitor deterioration of the turfgrass check sample. Thus, variability is incorporated in the future calibration to improve the accuracy and the validity of the NIRS measurements for turf.

The container in which the turf samples may be placed for test in an NIRS device is illustrated in FIG. 10 and generally by the designation 100. The preferred container is generally round in shape and has a slightly recessed top 101 which is optically transparent (e.g., a material which does not absorb light at the wavelengths of interest—such as glass or specific plastics). A plug element 102 is insertable into the bottom of the container 100 to seal a sample within the container 100. It will be appreciated that the container 100 has in inner circumference which forms a void within the container 100. The coloring of container 100 is preferably light absorbing (e.g., black) so as to not interfere with the test results.

The second set of data was also collected empirically. Variation among spectral signatures exists as patterns. Here the goal was to describe these patterns of variation, and represent the spectrum as a combination of these patterns. It will be appreciated that the principal components identify patterns; while the amount of a pattern in a particular spectrum is a score. The algorithms deployed are CENTER. This process allows ranking of samples according to their distance from the center of the group called global H.

A limit of 3.0 for H was used for the sample population and a *.PCA was generated. This file contains information needed to calculate the sample score, global H values and neighborhood H values.

The next step is to use a SELECT algorithm to identify samples that are similar and not needed for calibration because their neighborhoods are already represented by calibration samples. A neighborhood is defined as the space near a sample; it is; similar to global H, but is measured from a sample instead of group center. In the present case, a limit of 0.6 was selected. This process uses the *.PCA file to define sample neighborhoods and selects one sample per neighborhood. The selected sample is sent for wet chemistry reference values.

A calibration set of the sample spectra are were then used to generate a *.LIB file containing the scores for each sample. This file is used along with the *.PCA file to calculate the neighborhood H and global H values. Application of these two files in the satellite locations identifies samples beyond the scope of the calibration equations. This is how it was determined that generic equations (e.g. the Karsten system) do not have the necessary versatility. On the other hand, samples that were identified as outside of the calibration population can help improve the existing equations. This is considered an on-going process until all theoretical spectral variability, and the patterns are incorporated in the calibration population.

Calibration development is a process of building a mathematical relationship between reference values for each mineral arid the spectrum. In the present case, calibration was initiated using a combined mathematical treatment of each spectrum, SNV-Detrend; (Standard Normal Variance—takes each Spectrum and scales it to have standard deviation of 1.0. Detrend removes linear and quadratic curvature of each spectrum).

Figure 5:
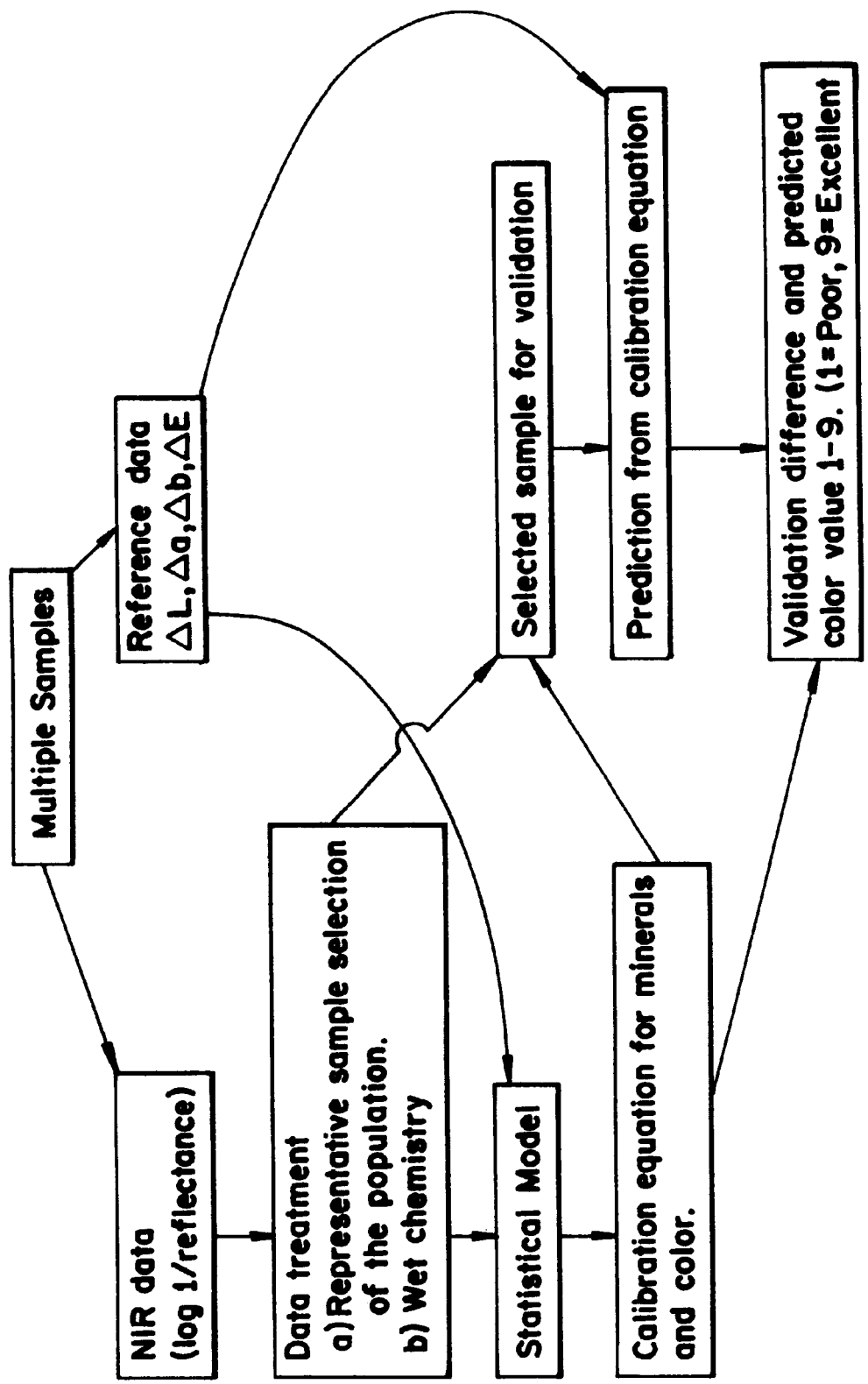
FIG. 5 shows a flow diagram of the process used to generate the statistical empirical color data from the turfgrass and from which the predictive equations are created and used.
Figure 8A:
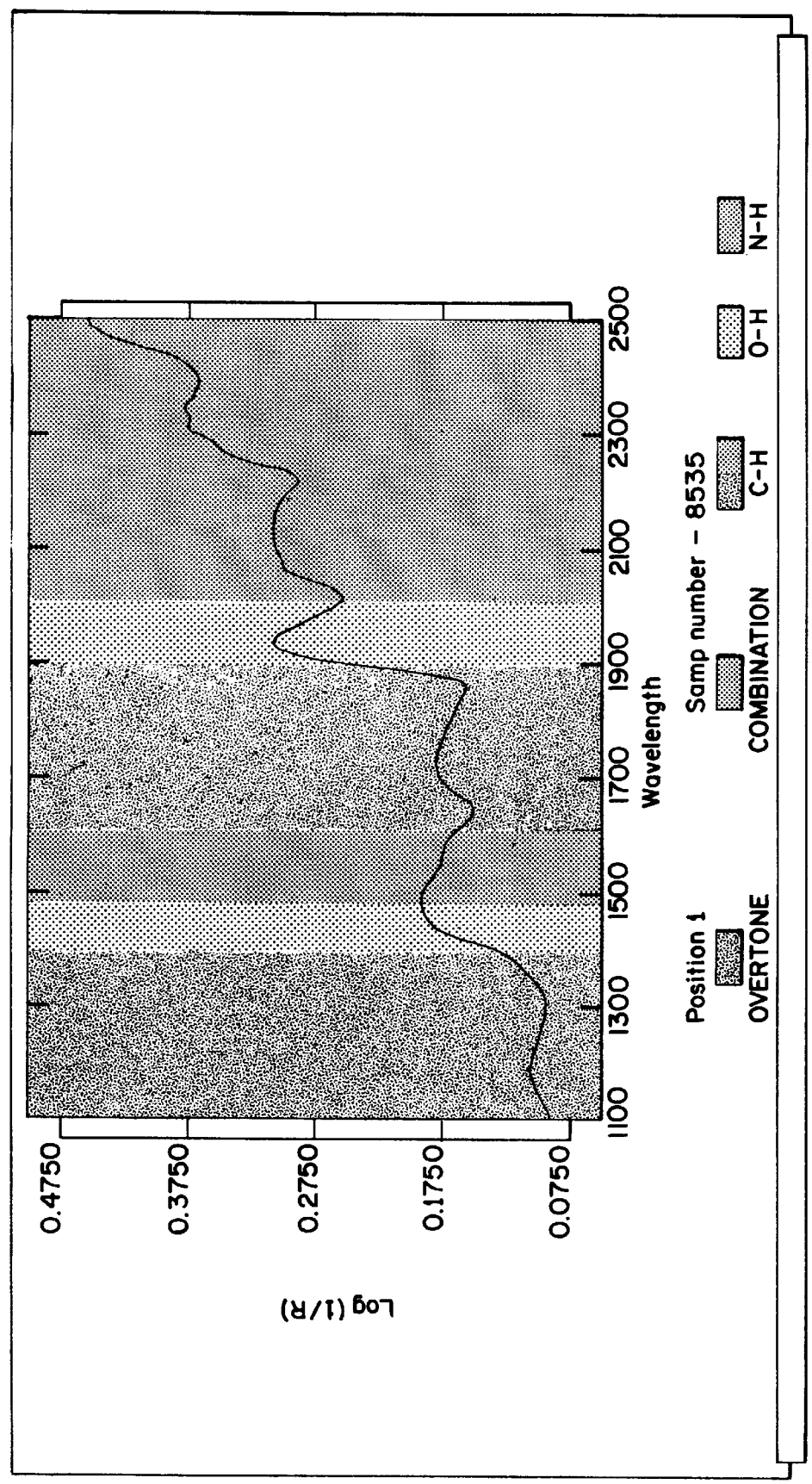
FIGS. 8a and 8b are representative graphs illustrating the spectral regions of interest and predictive equation coefficients in which moisture and nitrogen (among others) tend to occur.
Figure 8B:
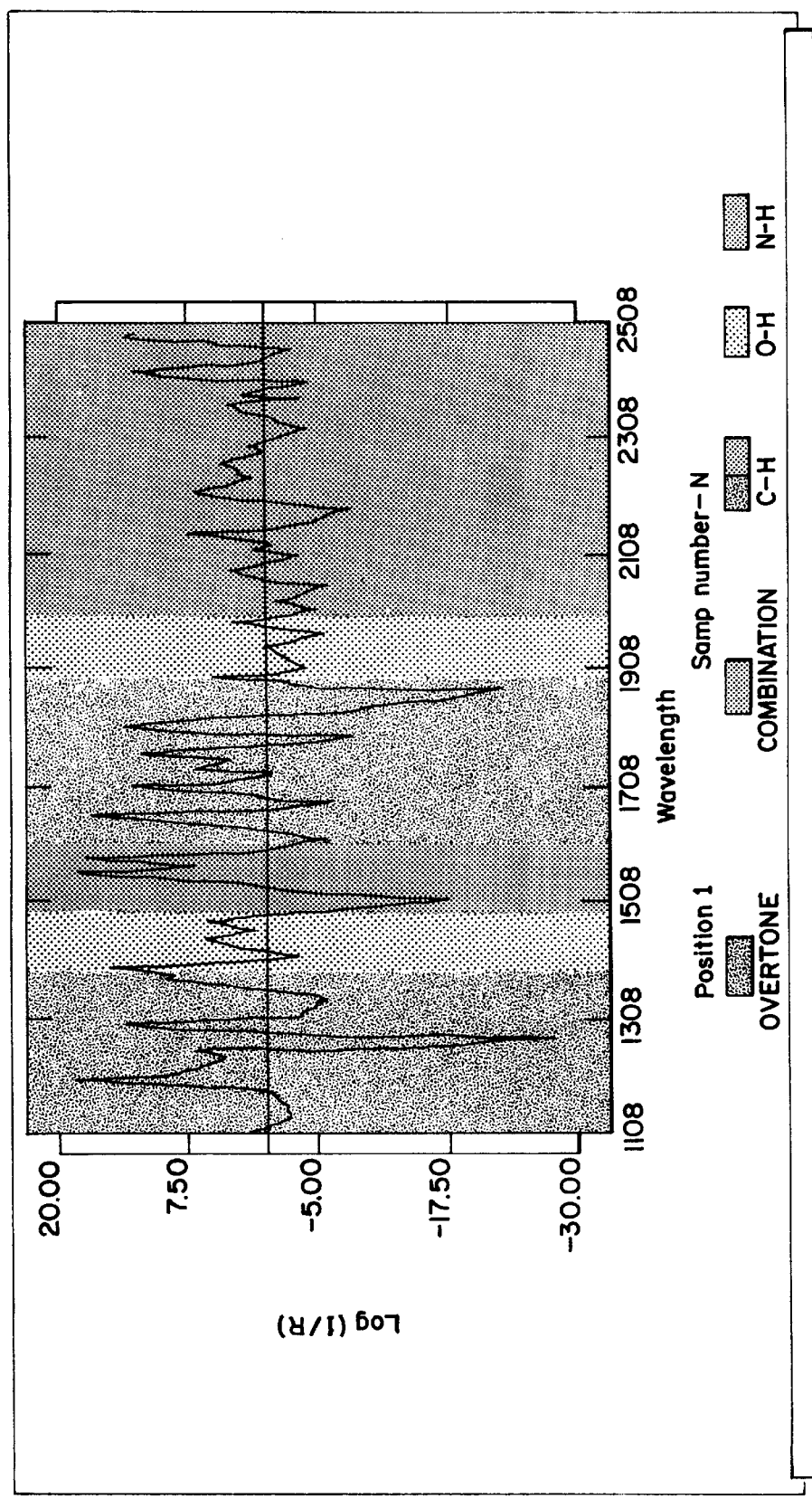

The math treatment used 1,4,4,1 (1=first derivative, 4=gap over which derivative is to be calculated, 4=first smoothing of points, 1=second smoothing of points). The spectral segment was 1100–2500 nm using every 4th wavelength using MPLS (Modified Partial Least Squares Regression or full spectrum regression). This method of regression uses all wavelengths identified in the segment to develop the equation. Literature suggests MPLS is more stable than others and the process offers cross validation to minimize overfitting of the equation. However, true tests of each equation are conducted by using a validation set of samples (e.g., samples that did not participate in the calibration set of samples). FIG. 5 illustrates the overall methodology of the empirical generation of the data, statistical models, and calibration equations. FIGS. 8a and 8b illustrate the results of taking the NIRS data and plotting it as a function of the log 1/R versus the wavelength. Also illustrated are regions where moisture and specific mineral content are exhibited.

c. Components and Operation

Turning now to FIG. 3, various hardware components comprising the quantitative color apparatus 50 (QCA) for use in performing NIRS analysis of turf color are illustrated in functional block form. The QCA 50 preferably includes a spectrophotometer 65.

At FIG. 2, a schematic overview of the field CM-525i detector 51 is provided. In the preferred embodiment, a spectrophotometer of the type manufactured by Minolta Company, Ltd., of Osaka Japan, under the model designation CM-500 series is used. However, other devices which provide spectral data might be used. The device 51 uses a xenon arc lamp 41 which is pulsed alter a sample 42 is located in a sample target area. The pulsed light enters an integrating sphere 43 resulting in diffuse illumination of the test object or sample 42. Light reflects off of the sample 42 back into the integrating sphere 43. A converging lens 44 gathers the reflected light onto a spectral sensor 45. The output from the spectral sensor is processed such that the device provides specific, reproducible color data in one of the several different spectral reflectance nomenclatures (e.g., XYZ or L*a*b*, among others).

The spectrophotometer 65 provides the output to a personal computer 52. The preferred spectrophotometer 65 is a NIRS system manufactured by Foss under the designation Model 5000 Monochronometer. Preferably the personal computer 52 is of the IBM compatible type (such as a computer with a Pentium chip). The operating software of such a system is preferably of the Windows 3.11, Windows 95 or Windows NT versions. However, other windows-style operating systems might be employed (e.g., Mcintosh operating systems).

The computer 52, generally includes a CPU 53 with random access memory (RAM) 54, a longer term memory storage device 55 (such as floppy disk, hard drive, or CD-style media), and such other attendant and peripheral devices so as to allow the processor to operate in its intended manner. The CPU block 53 communicates with the memory devices via bus 56. Also connected to the bus 56 is an interface card 58 which receives the optical data from the NIRS detector 65.

In the event that a remote computer(s) 61 are attached, then the CPU block 53 is able to communicates to remote computer(s) 61 through network card or modem device 59 and line 60. The line 60 may be hard-wired, may be a network connection, or may be a wide-area network connection over a leased or public phone line. It will also be appreciated that line 60 may include wireless communications devices. Use of a remote computer 61 may be beneficial to an end-user (e.g., results may be delivered directly), a supervisor or programmer may directly control computer 52 from a remote location, and/or provide for downloading of information, programming and/or diagnostics.

The IO device block 57 provides output for the visual display unit (VDU) 62. The VDU is preferably a cathode ray tube-style (CRT) display device. However, liquid crystal displays and other well known display devices might be employed. Operator input devices such as a keyboard, track ball and/or mouse are provided at block 63. A printer or other output device is provided at block 64.

Figure 4B:
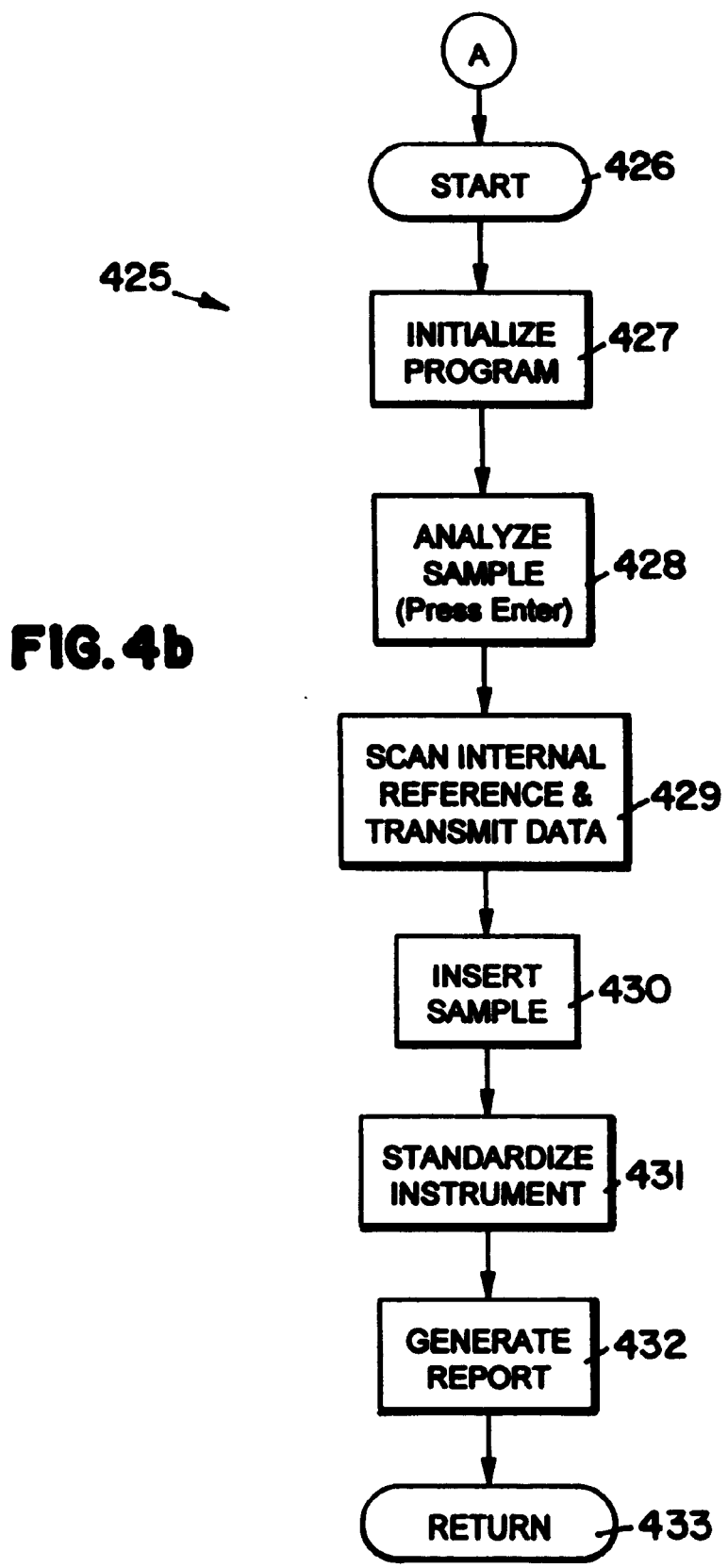
Figure 4C:
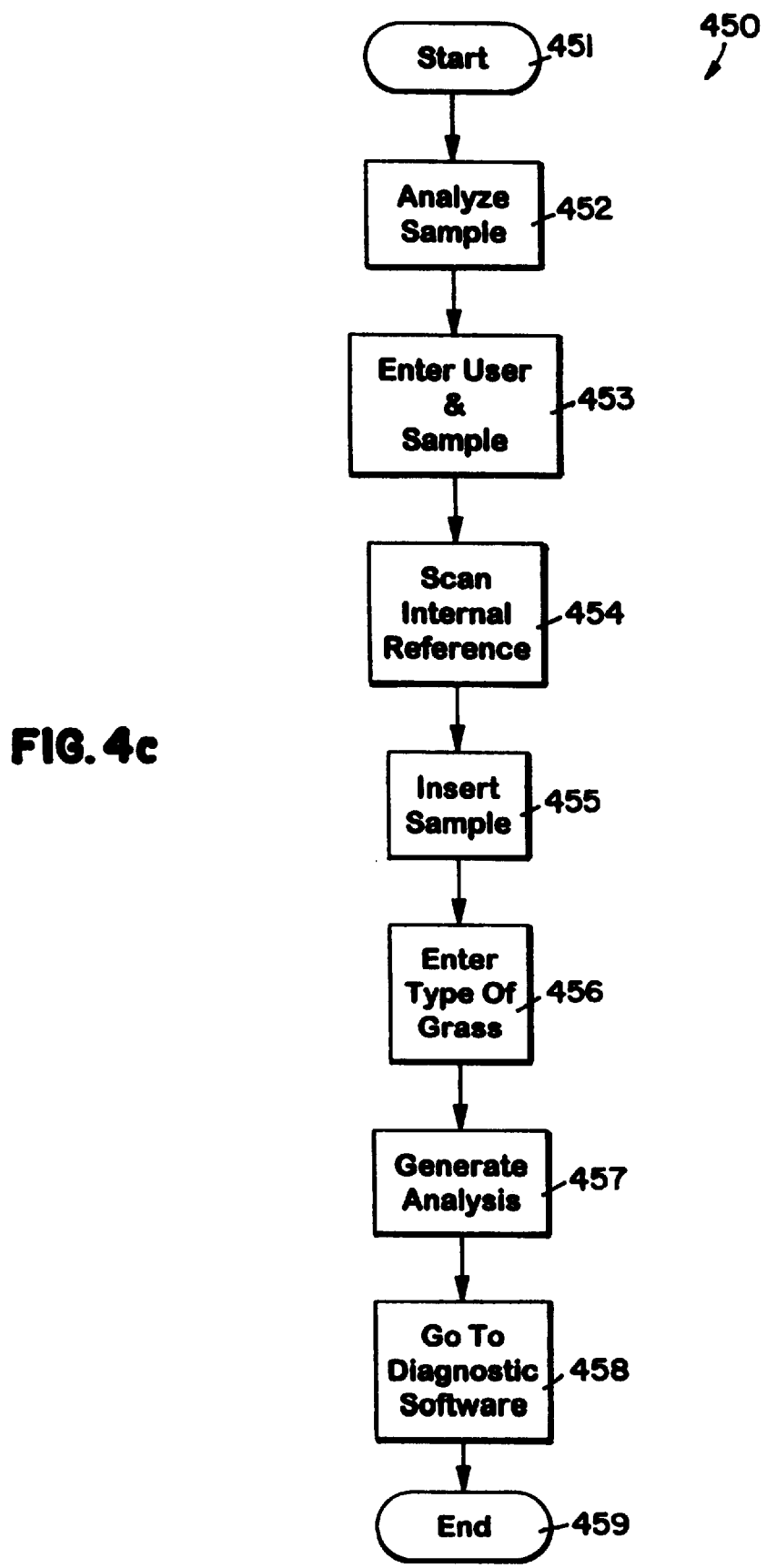

Turning now to FIGS. 4a, 4b, and 4c, various logical flow diagrams are illustrated. Software may be used to implement the logic flow. Such software may initially be resident in the memory storage device 55, may be downloaded from remote computer 61, or might be resident in an EPROM chip or board (not shown). The program shown generally at 400 may be run independently or be used as a module of another program.

The programming steps or logic flow associated with insuring the measurements of the optical device 65 and testing unknown samples is shown generally at 400. At 401 the process starts. Moving to block 402, the optical device (65) and its attendant equipment (e.g., PC 52) (referred to collectively by the designation 50) is turned on and initialized. The logic flow proceeds to block 403 for a warmup period in which the lamp of the detector 65 is turned on and stabilized. A sealed check sample is then requested at block 404. At this block, the verification routine illustrated in FIG. 4b occurs.

In FIG. 4b, the logical programming steps used to verify the repeatability of the test results of the device 65 is shown generally at the designation 425. The process starts at 426 and moves to block 427 where the program is initialized. A prompt occurs at block 428 to analyze the check sample and waits for a user response (here the "ENTER" key). When the correct response is entered by the operator, the logic flow proceeds to block 429 where an internal reference of the device is scanned and the resulting data is transmitted. A request to insert the sample occurs at block 430. When the sample is inserted, it is scanned at block 431 and standardized. The results are transmitted and a report is generated at block 432. The logic flow then returns to the main process of FIG. 4a from step 433.

Returning now to FIG. 4a, if the student T test is greater than 3 at block 405, then the lamp must be additionally stabilized and warmed up at block 403.

However, if the test is less than 3, then the process moves on to block 406 to begin testing unknown samples. To perform these tests of unknown samples, at block 407, optical data is collected and transmitted to the computer 52 at block 408. Optical data is predicted with the predeveloped equations at block 409. The process then moves to block 410 where the predicted data is transmitted to the database and a report is generated. At block 411 if a user wishes to perform another test on an unknown sample, the logic flow returns to block 406. If no further samples are desired, then the system is powered down to block 412 and ends at block 413. In the preferred embodiment, while the data, quality tests, predetermined equations and the like are developed empirically, software which handles the I/O functions (including the optical device 65), data bases and optical data is commercially available. Such software is manufactured by Infrasoft International under the designation SCAN.EXE Version 3.0.

FIG. 4c, the logical processing steps taken to analyze the sample are expanded generally at the designation 450. Here, the process starts at 451 and moves to 452 where a request to analyze a sample (by collecting light reflected from the sample) by device 65 is entered by a user. The user and sample number are collected at block 453 while the internal reference is scanned at 454. Moving to block 455, the device waits for the sample to be inserted. The type of grass is inserted at block 456 so that an accurate analysis may be generated at block 457. The results of the analysis are sent to the diagnostic software at block 458 and the process ends at block 459.

A commercially available diagnostic software which accepts the analysis and generates a predictive report is manufactured by The Toro Company, the Assignee of the present invention, under the designation TORO Diagnostic Software (Version 2.40). An example of the reports which can be generated by such software is illustrated in FIGS. 9a through 9b and FIGS. 9c through 9g.

Figure 9B:
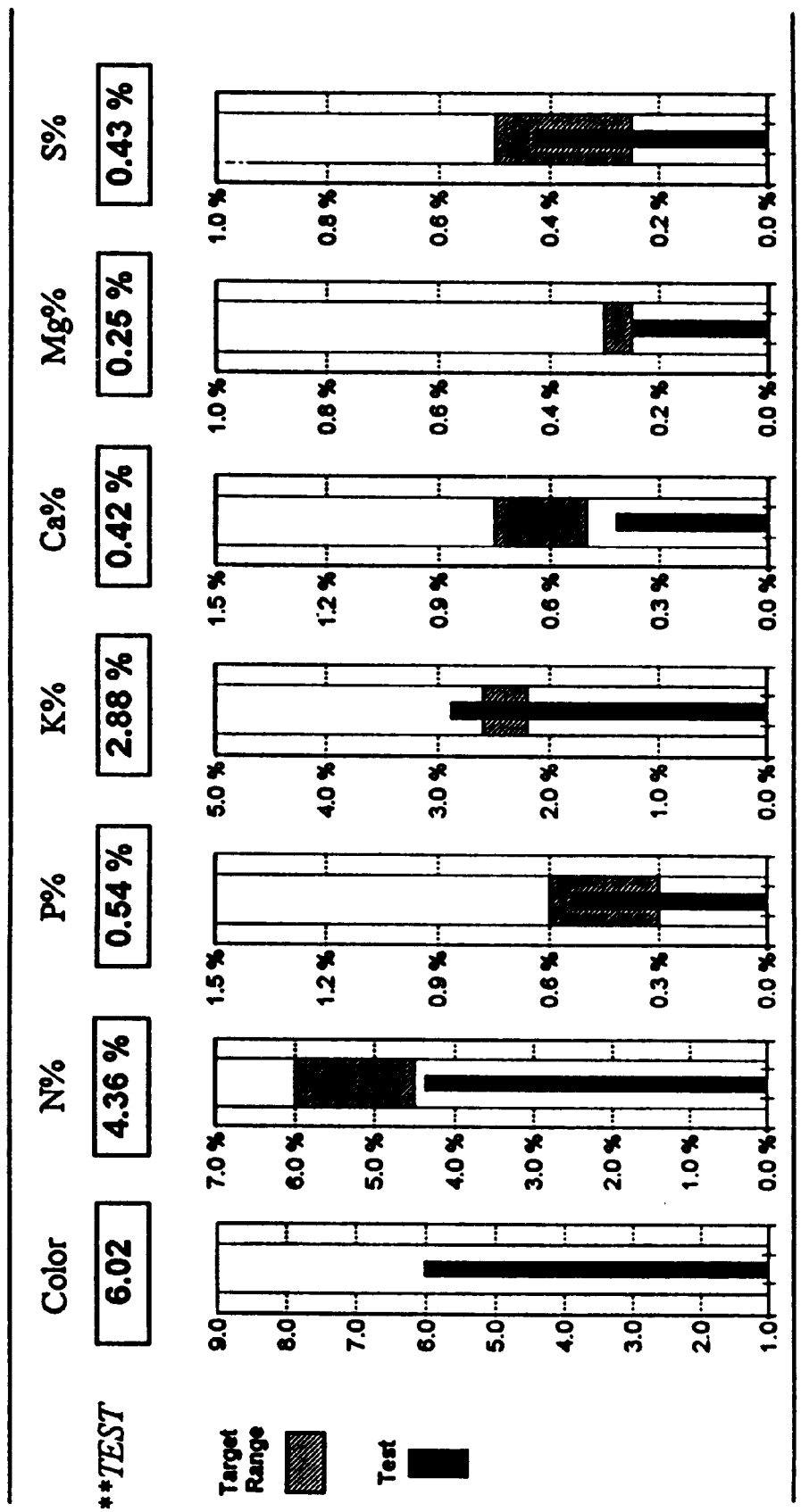
Figure 9E:
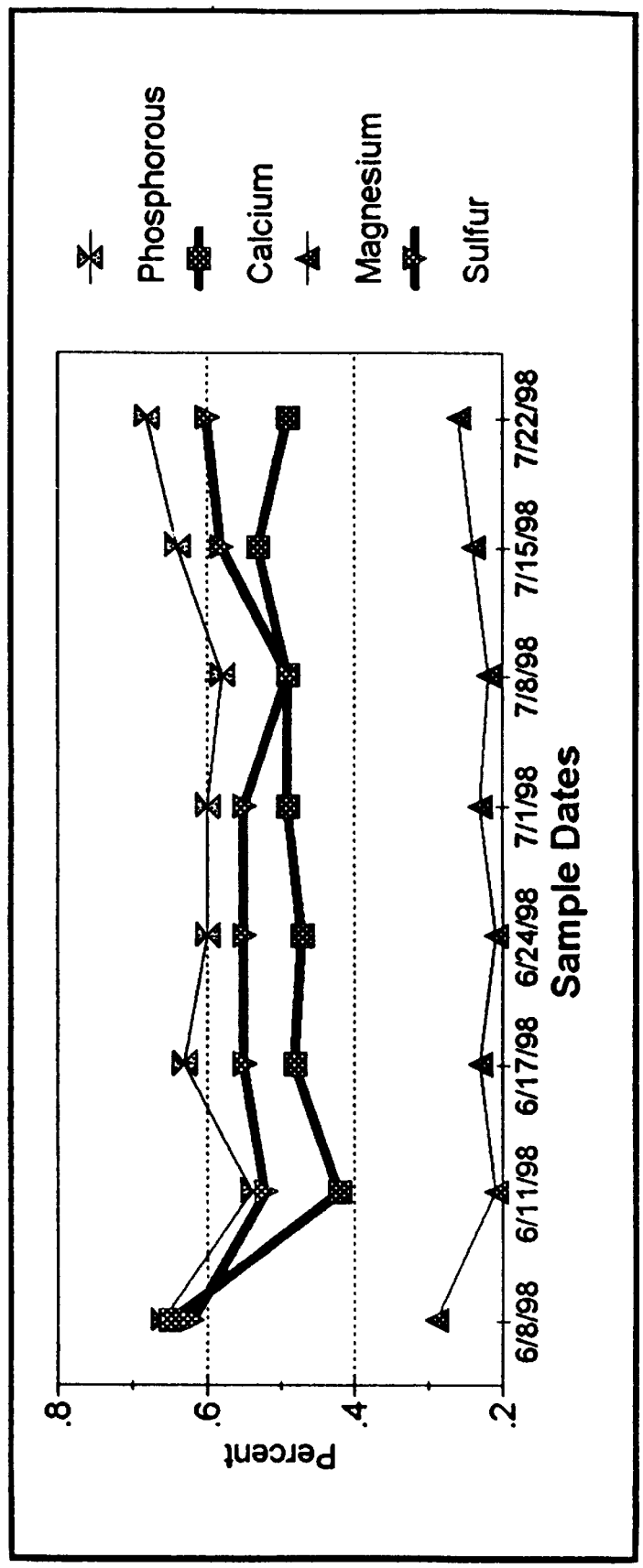
Figure 9F:
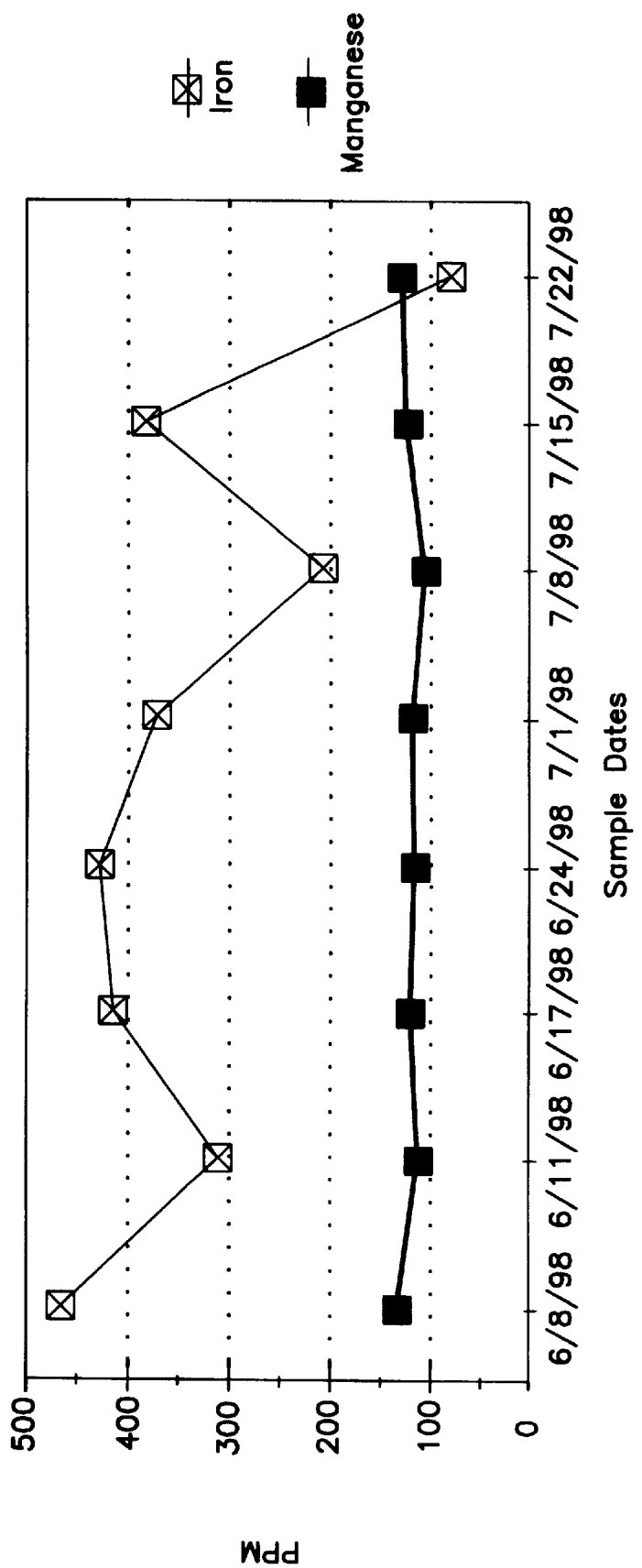
Figure 9G:
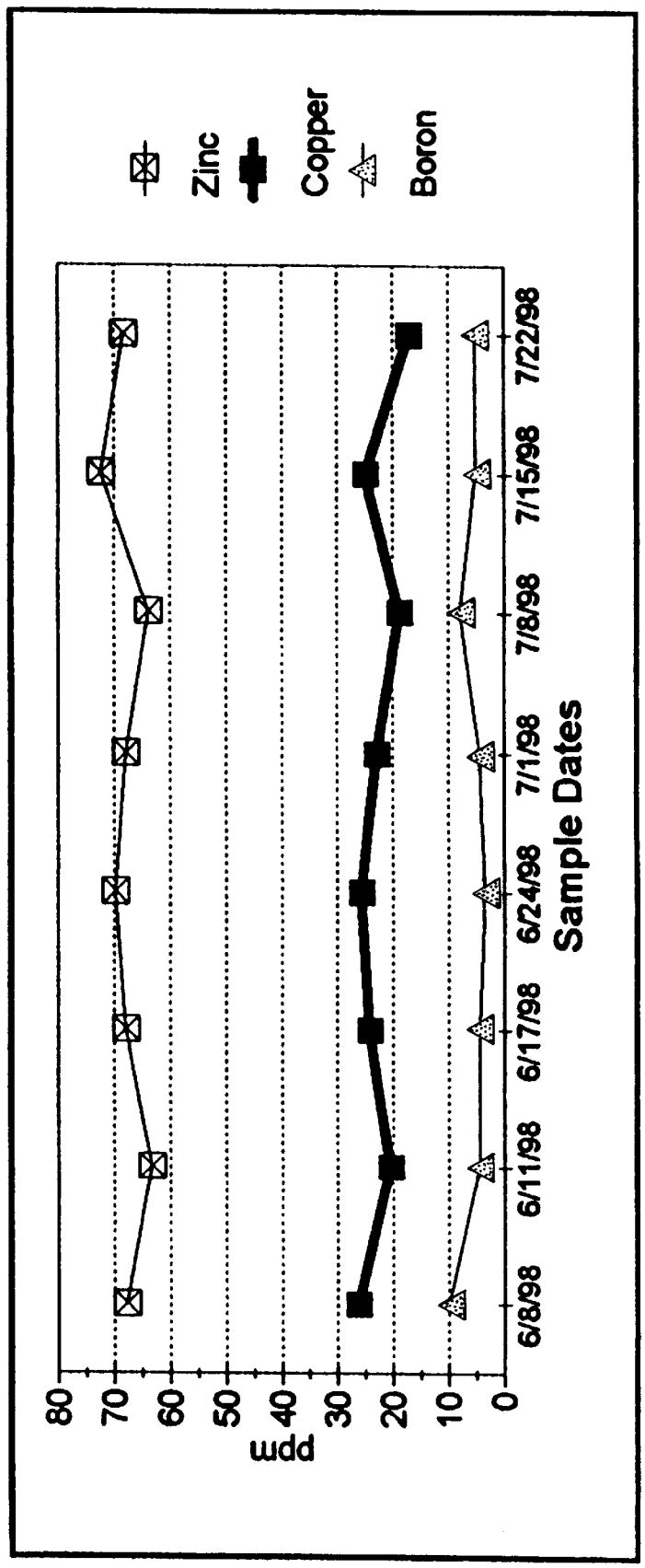

Turning first to FIGS. 9a through 9b, an NIRS Tissue Analysis Report is illustrated. The report is based on a test sample which is creeping bentgrass taken on a certain date and from a certain location (in this example the sixth green at the XYZ Golf Course). From the NIRS color analysis, a report on a variety of minerals is generated and includes high ranges, low ranges, target ranges and the actual test range.

Figure 7A:
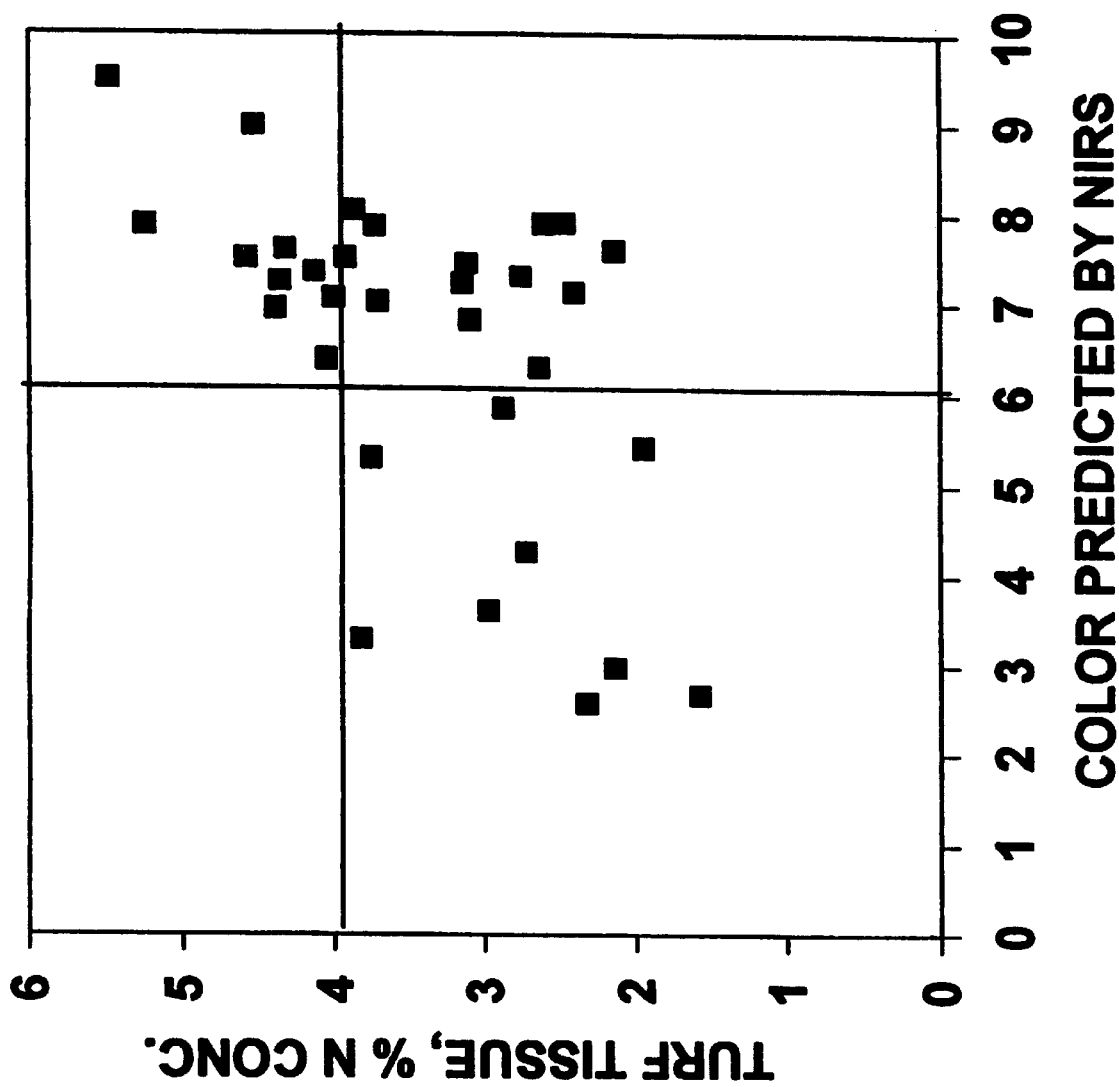
FIG. 7a is a representative graph of a stored data set of the concentration of nitrogen as a percentage of turf tissue versus the color predicted by NIRS.
Figure 7B:
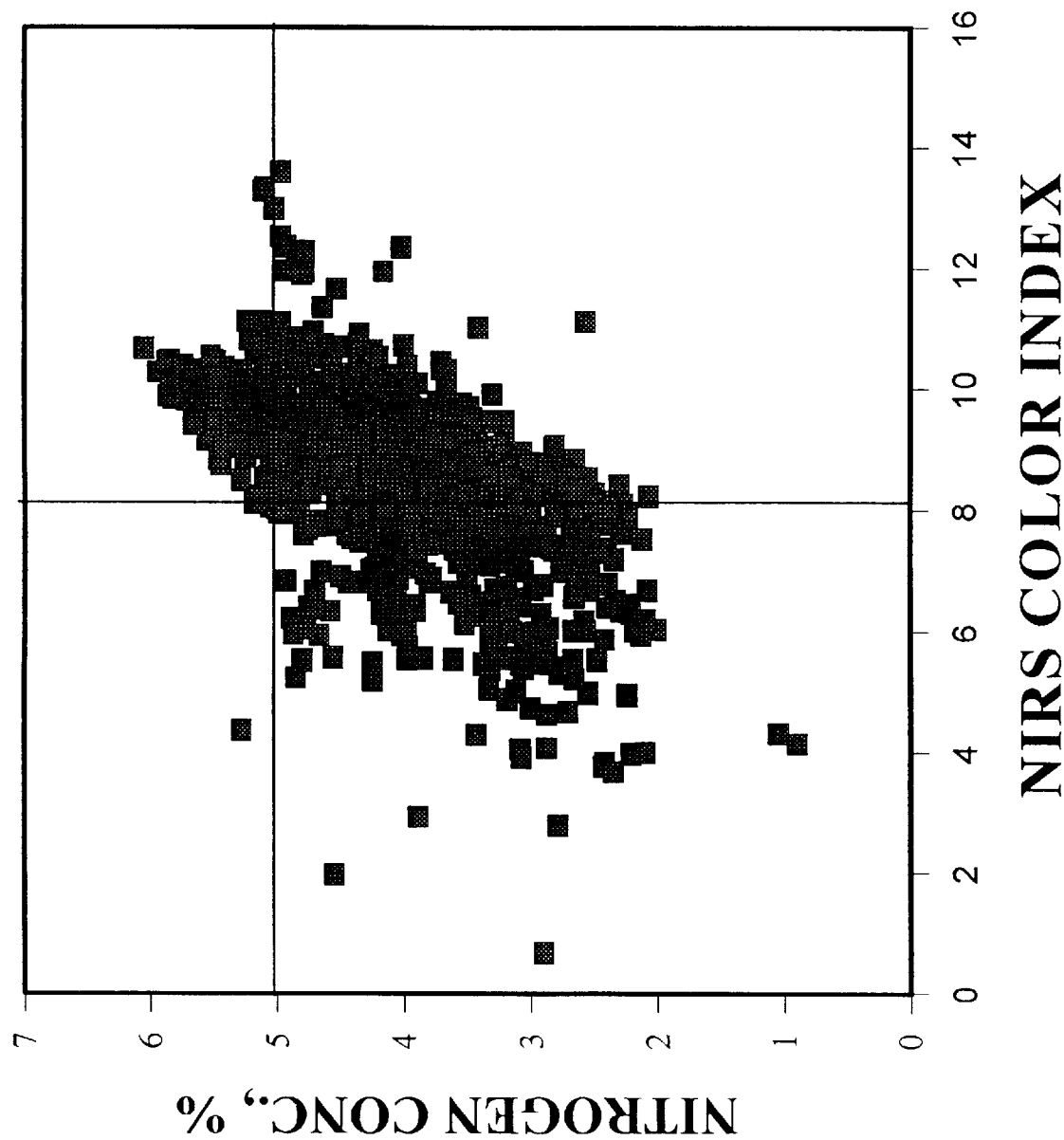
FIG. 7b is a representative graph of a flattened set of data points of the general relationship between nitrogen as a concentration percentage and the NIRS color index.

Turning to FIGS. 9c through 9g, a NIRS Trend Analysis is illustrated. Here the target ranges are shown over time from which trends can be detected and the actual results of treatment programs analyzed. It will be appreciated that together with the reports shown in FIGS. 9a through 9b and FIGS. 9c through 9g, the relationship between color and nitrogen concentration (by way of example) shown in FIGS. 7a and 7b, may be employed to determine whether color may be improved for that sample of turf grass by varying the nitrogen concentration. The coefficients of the equations are preferably generated for different types of grass (and/or the same or similar types of grass in differing geographical locations) so as to reduce the blending of the statistical models. Similarly, by testing different parts of the turf grass separately, unneeded chemical applications may be avoided.

d. Working Example

Figure 12:
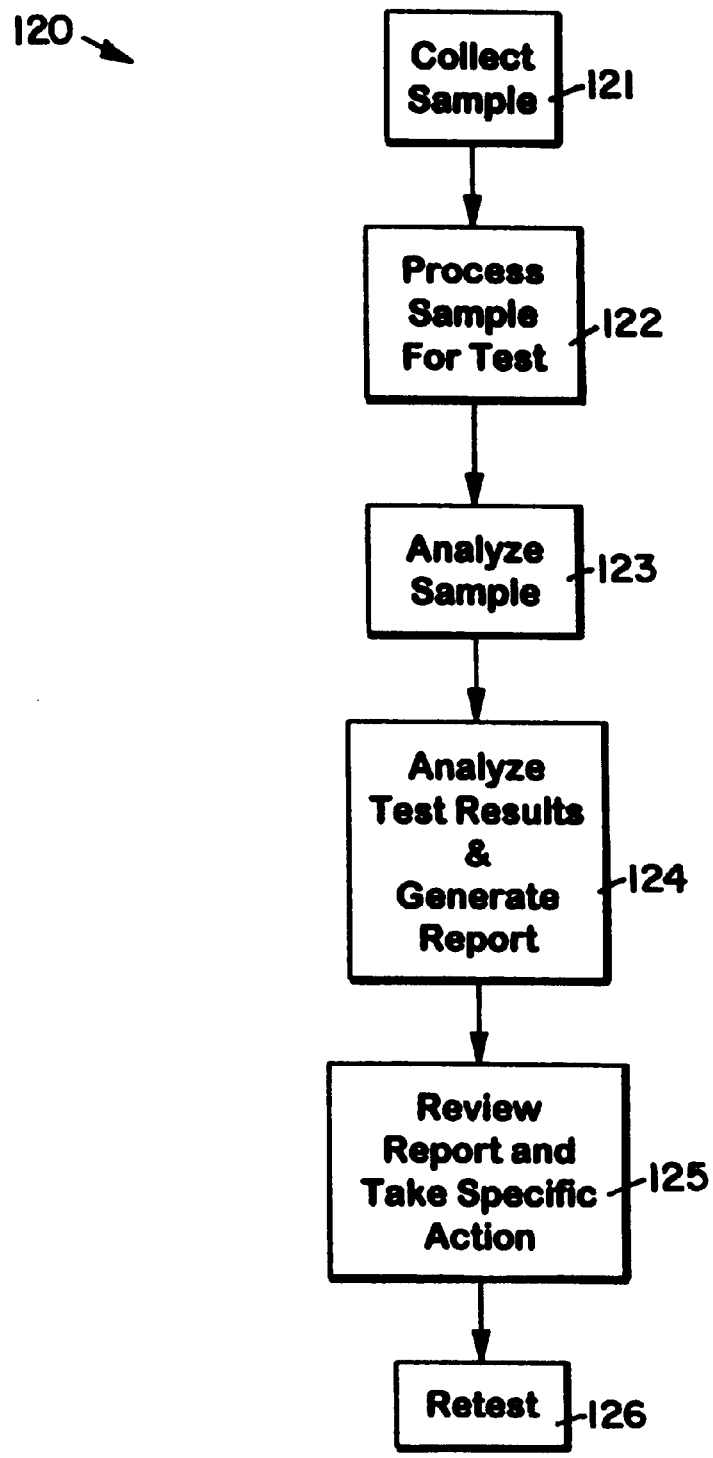
FIG. 12 is diagram of the method steps in which the present invention may be employed by a groundskeeper in the analysis of turf grass.

FIG. 12 illustrates a working example in which the principles of the present invention may be employed in a turf grass setting. The process is shown generally by the designation 120 and starts at block 121 where a specific sample is taken by a grounds keeper or other individual interested in analyzing turf grass. Generally the collected sample be comprised of freshly mowed clippings from the turf grass of interest.

The sample is next provided to a testing group at block 122 to process the sample. The testing group preferably has equipment which operates in accordance with device 50 of FIG. 3 (described above). The sample is prepared as outlined in Table 2 above and is then placed and sealed within a container 100 (best seen in FIG. 10).

At block 123, the sample is analyzed as discussed in connection with FIGS. 4a, 4b and 4c above. The test results are analyzed at block 124 and appropriate reports generated, such as those set forth in FIGS. 9a and 9b. If the grounds keeper or individual has a computer (e.g., remote computer 61), then the test results may be directly communicated to the computer via modem 59. Alternatively, the tests may be printed on printer 64 and forwarded to the user.

At block 125 the report is reviewed and specific action may be taken as a result to improve levels of minerals and/or to adjust levels of minerals to change the color. For example, the report may include a predictive outcome for application of additional nitrogen to the turf grass. As noted, FIGS. 7a and 7b indicate a relationship between nitrogen concentration and color. From this relationship, it may be determined if color may be improved by addition of nitrogen for the specific turfgrass. Also, it can be determined if the color cannot be improved by adding nitrogen and/or if excessive nitrogen is being applied which is not benefiting the turfgrass color (in which case the applications may be reduced). Therefore, the grounds keeper or individual can act on the predictive actions and retest at block 126 periodically to develop a trend and confirm the recommended report actions.

Preferred embodiments of the invention are described above. Those skilled in the art will recognize that many embodiments are possible within the scope of the invention. Variations and modifications of the various parts and assemblies can certainly be made and still fall within the scope of the invention. Thus, the invention is limited only to the apparatus and method recited in the following claims, and equivalents thereto.

What is claimed is:

1. A method for determining the color of a sample of turf grass, comprising the steps of:
   a) storing a first value set of data relating to the color of turfgrass;
   b) measuring the near infrared reflectance spectroscopy of the sample turfgrass;
   c) generating a photometric output signal;
   d) receiving the generated output signal;
   e) comparing the received signal to the first value set of data; and
   f) predicting a quantitative color value of the sample turfgrass.

2. The method of claim 1, further comprising the steps of:
   a) storing a second value set of data relating to a specific mineral content of turfgrass resulting from color; and
   b) comparing the determined quantitative color value of the sample turfgrass to the data in the second value set of data; and
   c) determining a predictive outcome of application of the specific mineral to the turfgrass, wherein the turfgrass quality may be optimized.

3. The method of claim 2, further comprising the step of applying the specific mineral to the turfgrass based on the predictive outcome.

* * * * *